(12) United States Patent
Moffitt et al.

(10) Patent No.: US 8,560,085 B2
(45) Date of Patent: Oct. 15, 2013

(54) METHODS FOR MAKING LEADS WITH SEGMENTED ELECTRODES FOR ELECTRICAL STIMULATION SYSTEMS

(75) Inventors: Michael Adam Moffitt, Valencia, CA (US); Anne Margaret Pianca, Santa Monica, CA (US); Andrew DiGiore, San Francisco, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/369,013

(22) Filed: Feb. 8, 2012

(65) Prior Publication Data

US 2012/0203321 A1  Aug. 9, 2012

Related U.S. Application Data

(60) Provisional application No. 61/440,533, filed on Feb. 8, 2011.

(51) Int. Cl.
*A61N 1/00* (2006.01)

(52) U.S. Cl.
USPC ........................................................ 607/116

(58) Field of Classification Search
USPC ................................................. 607/115–139
See application file for complete search history.

(56) References Cited

U.S. PATENT DOCUMENTS

| | | | |
|---|---|---|---|
| 4,602,624 A | 7/1986 | Naples et al. | |
| 4,630,611 A | 12/1986 | King | |
| 4,744,370 A | 5/1988 | Harris | |
| 5,000,194 A | 3/1991 | van den Honert et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

International Search Report and Written Opinion, PCT/US2012/024309, mailed Aug. 20, 2012.

(Continued)

*Primary Examiner* — Scott Getzow
(74) *Attorney, Agent, or Firm* — Frommer Lawrence & Haug LLP; Bruce E. Black

(57) ABSTRACT

One embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes. At least a first portion of the lead body, proximal to the electrodes, is transparent or translucent and at least a second portion of the lead body, separating two or more of the segmented electrodes, is opaque so that the segmented electrodes separated by the second portion of the lead body are visually distinct. Alternatively or additionally, the stimulation lead can include an indicator ring, a stripe, a groove, or a marking aligned with one or more of the segmented electrodes.

15 Claims, 9 Drawing Sheets

(56) References Cited

U.S. PATENT DOCUMENTS

| | | |
|---|---|---|
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,809,446 B2 | 10/2010 | Meadows |
| 7,840,188 B2 | 11/2010 | Kurokawa |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 | 9/2008 | Farah et al. |
| 2009/0187222 A1 | 7/2009 | Barker |
| 2009/0204192 A1 | 8/2009 | Carlton et al. |
| 2009/0204193 A1 | 8/2009 | Kokones et al. |
| 2009/0276021 A1 | 11/2009 | Meadows |
| 2010/0036468 A1 | 2/2010 | Decre et al. |
| 2010/0076535 A1 | 3/2010 | Pianca |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |

FOREIGN PATENT DOCUMENTS

| | | |
|---|---|---|
| EP | 0832867 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009102536 A1 | 8/2009 |

OTHER PUBLICATIONS

U.S. Appl. No. 12/177,823, filed Jul. 22, 2008.
U.S. Appl. No. 13/275,112, filed Oct. 17, 2011.
U.S Appl. No. 13/363,059, filed Jan. 31, 2012.
U.S. Appl. No. 13/368,982, filed Feb. 8, 2012.
U.S. Appl. No. 13/368,733, filed Feb. 8, 2012.
U.S. Appl. No. 13/787,171, filed Mar. 6, 2013.
U.S. Appl. No. 13/750,725, filed Jan. 25, 2013.
U.S. Appl. No. 13/899,316, filed May 21, 2013.
U.S. Appl. No. 13/906,776, filed May 31, 2013.

METHODS FOR MAKING LEADS WITH SEGMENTED ELECTRODES FOR ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 61/440,533 filed on Feb. 8, 2011, which is incorporated herein by reference.

FIELD

The invention is directed to the area of electrical stimulation systems and methods of making and using the systems. The present invention is also directed to electrical stimulation leads with multiple sets of segmented electrodes, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes. Optionally, at least some of the segmented electrodes are formed into a first set of segmented electrodes having at least two of the segmented electrodes disposed around a circumference of the lead at a first longitudinal position along the lead, and a second set of segmented electrodes having at least two of the segmented electrodes disposed around a circumference of the lead at a second longitudinal position along the lead. At least a first portion of the lead body, proximal to the electrodes, is transparent or translucent and at least a second portion of the lead body, separating two or more of the segmented electrodes, is opaque so that the segmented electrodes separated by the second portion of the lead body are visually distinct.

Another embodiment is a stimulation lead including a lead body having a longitudinal surface, a distal end, and a proximal end; and multiple electrodes disposed along the longitudinal surface of the lead body near the distal end of the lead body. The multiple electrodes include multiple segmented electrodes. Optionally, at least some of the segmented electrodes are formed into a first set of segmented electrodes having at least two of the segmented electrodes disposed around a circumference of the lead at a first longitudinal position along the lead. The stimulation lead also includes an indicator ring disposed distal to the electrodes and marked to indicate a one of the segmented electrodes.

Yet another embodiment is a stimulation lead including a lead body having a longitudinal surface, a distal end, and a proximal end; and multiple electrodes disposed along the longitudinal surface of the lead body near the distal end of the lead body. The multiple electrodes include multiple segmented electrodes. At least some of the segmented electrodes are formed into a first set of segmented electrodes having at least two of the segmented electrodes disposed around a circumference of the lead at a first longitudinal position along the lead, and a second set of segmented electrodes having at least two of the segmented electrodes disposed around a circumference of the lead at a second longitudinal position along the lead. The first and second sets of segmented electrodes are adjacent to each other and aligned with each other. The stimulation lead also includes a stripe extending along at least a distal portion of the lead body and aligned with a one of the segmented electrodes in each of the first and second sets of segmented electrodes.

A further embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes. At least some of the segmented electrodes are formed into a first set of segmented electrodes having at least two of the segmented electrodes disposed around a circumference of the lead at a first longitudinal position along the lead, and a second set of segmented electrodes having at least two of the segmented electrodes disposed around a circumference of the lead at a second longitudinal position along the lead. The first and second sets of segmented electrodes are adjacent to each other and aligned with each other. The stimulation lead also includes a groove formed in the lead body and extending along at least a distal portion of the lead body. The groove is aligned with a one of the segmented electrodes in each of the first and second sets of segmented electrodes.

Another embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes. At least some of the segmented electrodes are formed into a first set of segmented electrodes having at least two of the segmented electrodes disposed around a circumference of the lead at a first longitudinal position along the lead, and a second set of segmented electrodes having at least two of the segmented electrodes disposed around a circumference of the lead at a second longitudinal position along the lead. The first and second sets of segmented electrodes are adjacent to each other and aligned with each other. The stimulation lead also includes a marking disposed at or near the distal end of the lead body and distal to all of the electrodes. The marking is aligned with a one of the segmented electrodes in each of the first and second sets of segmented electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to forming electrical stimulation leads with multiple sets of segmented electrodes, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position.

A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes. For illustrative purposes, the leads are described herein relative to use for deep brain stimulation, but it will be understood that any of the leads can be used for applications other than deep brain stimulation.

Deep brain stimulation devices and leads are described in, for example, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, U.S. Patent Application Publication No. 2009/0187222 A1, and U.S. Patent Application Ser. No. 61/426,784. Each of these references is incorporated herein by reference.

Figure 1:
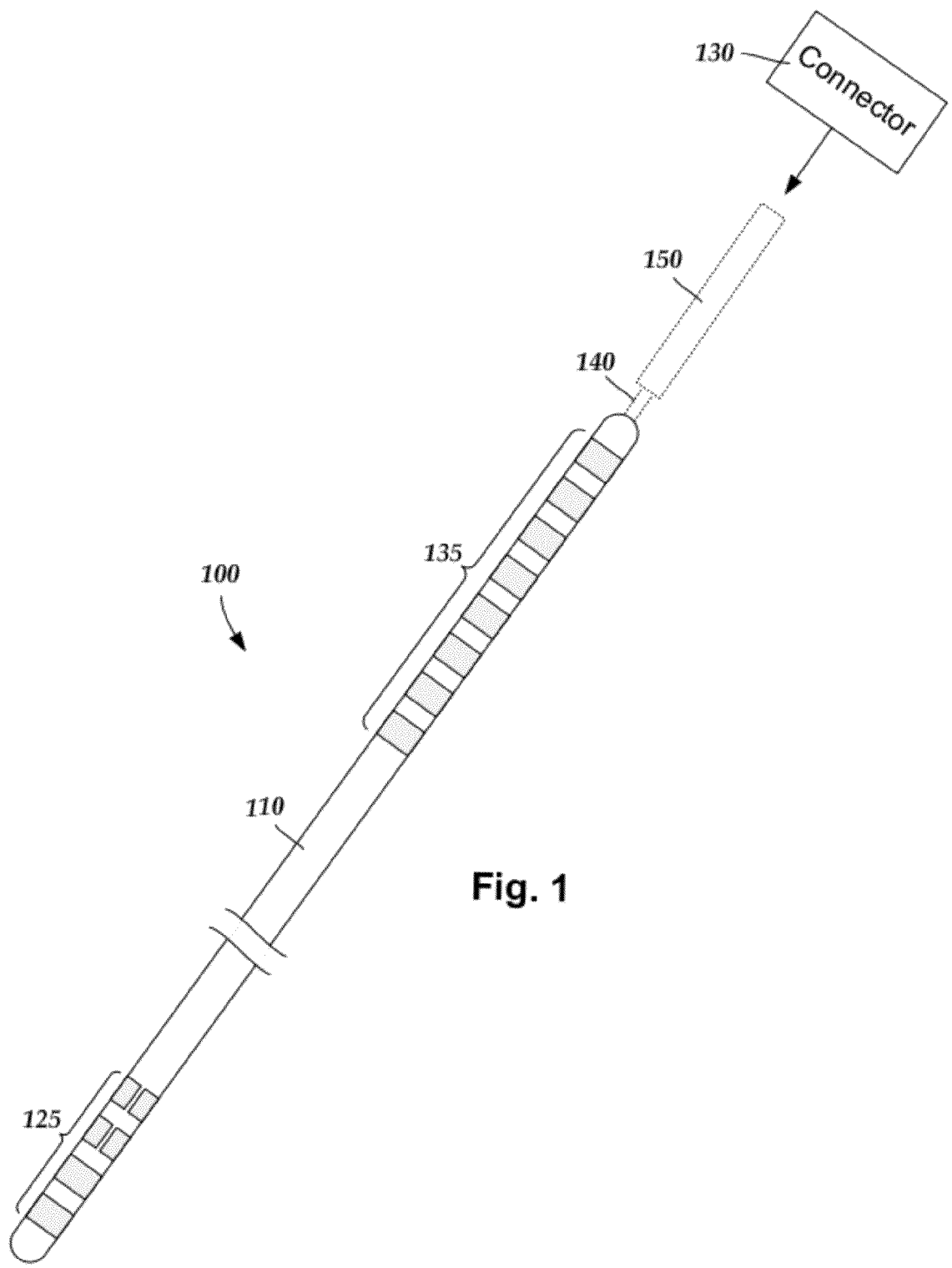
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more than eight stimulation channels (e.g., 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

Figure 2:
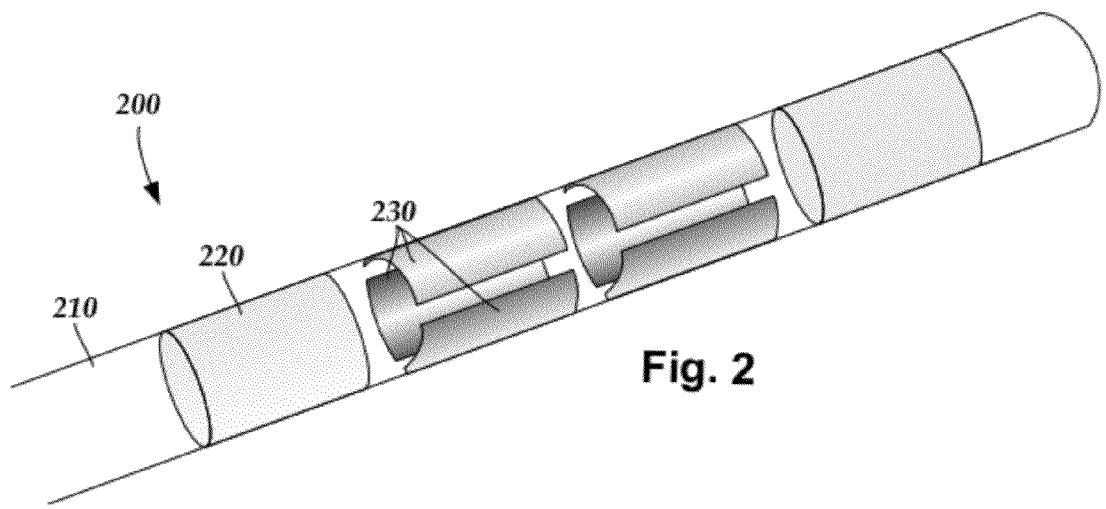
FIG. 2 is a schematic perspective view of one embodiment of a portion of a lead having a plurality of segmented electrodes, according to the invention.

FIG. 2 illustrates one embodiment of a distal portion of a lead 200 for brain stimulation. The lead 200 includes a lead body 210, one or more optional ring electrodes 220, and a plurality of sets of segmented electrodes 230. The lead body 210 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 200 may be in contact with body tissue for extended periods of time. In at least some embodiments, the lead 200 has a cross-sectional diameter of no more than 1.5 mm and may be in the range of 1 to 1.5 mm. In at least some embodiments, the lead 200 has a length of at least 10 cm and the length of the lead 200 may be in the range of 25 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 220 may be disposed on any part of the lead body 210, usually near a distal end of the lead 200. In FIG. 2, the lead 200 includes two ring electrodes 220. Any number of ring electrodes 220 may be disposed along the length of the lead body 210 including, for example, one, two three, four, five, six, seven, eight, nine, ten, eleven, twelve, thirteen, fourteen, fifteen, sixteen or more ring electrodes 220. It will be understood that any number of ring electrodes may be disposed along the length of the lead body 210. In some embodiments, the ring electrodes 220 are substantially cylindrical and wrap around the entire circumference of the lead body 210. In some embodiments, the outer diameters of the ring electrodes 220 are substantially equal to the outer diameter of the lead body 210. The length of the ring electrodes 220 may vary according to the desired treatment and the location of the target neurons. In some embodiments the length of the ring electrodes 220 are less than or equal to the diameters of the ring electrodes 220. In other embodiments, the lengths of the ring electrodes 220 are greater than the diameters of the ring electrodes 220.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

In FIG. 2, the lead 200 is shown having a plurality of segmented electrodes 230. Any number of segmented electrodes 230 may be disposed on the lead body 210 including, for example, one, two three, four, five, six, seven, eight, nine, ten, eleven, twelve, thirteen, fourteen, fifteen, sixteen or more segmented electrodes 230. It will be understood that any number of segmented electrodes 230 may be disposed along the length of the lead body 210.

The segmented electrodes 230 may be grouped into sets of segmented electrodes, where each set is disposed around a circumference of the lead 200 at a particular longitudinal portion of the lead 200. The lead 200 may have any number of segmented electrodes 230 in a given set of segmented electrodes. The lead 200 may have one, two, three, four, five, six, seven, eight, or more segmented electrodes 230 in a given set. In at least some embodiments, each set of segmented electrodes 230 of the lead 200 contains the same number of segmented electrodes 230. The segmented electrodes 230 disposed on the lead 200 may include a different number of electrodes than at least one other set of segmented electrodes 230 disposed on the lead 200.

The segmented electrodes 230 may vary in size and shape. In some embodiments, the segmented electrodes 230 are all of the same size, shape, diameter, width or area or any combination thereof. In some embodiments, the segmented electrodes 230 of each circumferential set (or even all segmented electrodes disposed on the lead 200) may be identical in size and shape.

Each set of segmented electrodes 230 may be disposed around the circumference of the lead body 210 to form a substantially cylindrical shape around the lead body 210. The spacing between individual electrodes of a given set of the segmented electrodes may be the same, or different from, the spacing between individual electrodes of another set of segmented electrodes on the lead 200. In at least some embodiments, equal spaces, gaps or cutouts are disposed between each segmented electrode 230 around the circumference of the lead body 210. In other embodiments, the spaces, gaps or cutouts between the segmented electrodes 230 may differ in size or shape. In other embodiments, the spaces, gaps, or cutouts between segmented electrodes 230 may be uniform for a particular set of the segmented electrodes 230, or for all sets of the segmented electrodes 230. The sets of segmented electrodes 230 may be positioned in irregular or regular intervals along a length the lead body 210.

Conductor wires that attach to the ring electrodes 220 or segmented electrodes 230 extend along the lead body 210. These conductor wires may extend through the material of the lead 200 or along one or more lumens defined by the lead 200, or both. The conductor wires are presented at a connector (via terminals) for coupling of the electrodes 220, 230 to a control unit (not shown).

Figure 3A:
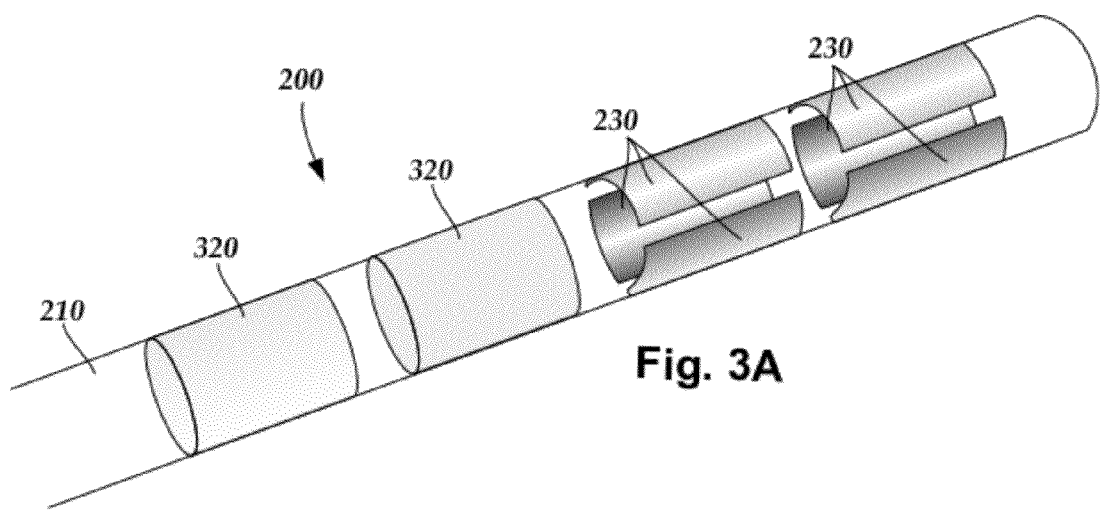
FIG. 3A is a perspective view of a third embodiment of a portion of a lead having a plurality of segmented electrodes, according to the invention.
Figure 3B:
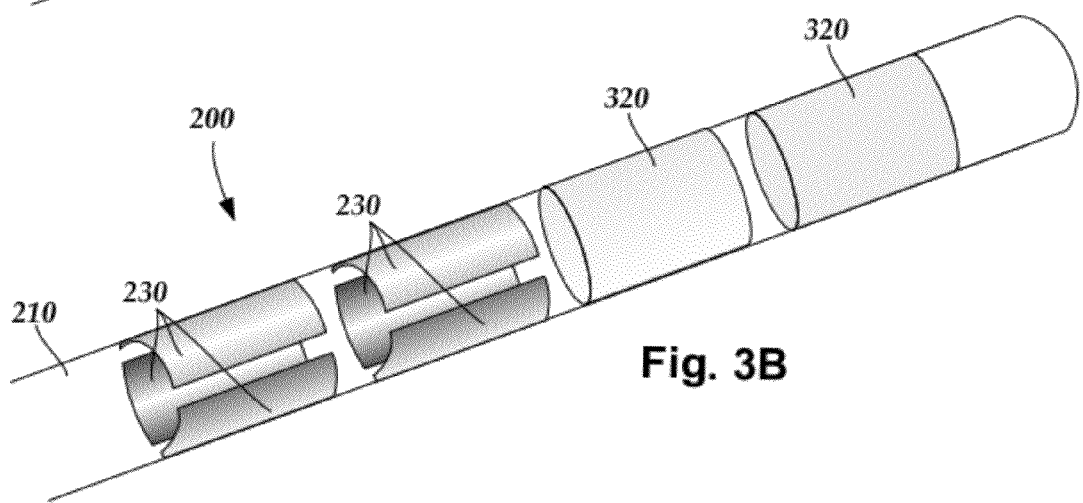
FIG. 3B is a perspective view of a fourth embodiment of a portion of a lead having a plurality of segmented electrodes, according to the invention.

When the lead 200 includes both ring electrodes 220 and segmented electrodes 230, the ring electrodes 220 and the segmented electrodes 230 may be arranged in any suitable configuration. For example, when the lead 200 includes two sets of ring electrodes 220 and two sets of segmented electrodes 230, the ring electrodes 220 can flank the two sets of segmented electrodes 230 (see e.g., FIG. 2). Alternately, the two sets of ring electrodes 220 can be disposed proximal to the two sets of segmented electrodes 230 (see e.g., FIG. 3A), or the two sets of ring electrodes 220 can be disposed distal to the two sets of segmented electrodes 230 (see e.g., FIG. 3B). It will be understood that other configurations are possible as well (e.g., alternating ring and segmented electrodes, or the like).

By varying the location of the segmented electrodes 230, different coverage of the target neurons may be selected. For example, the electrode arrangement of FIG. 3A may be useful if the physician anticipates that the neural target will be closer to a distal tip of the lead body 210, while the electrode arrangement of FIG. 3B may be useful if the physician anticipates that the neural target will be closer to a proximal end of the lead body 210.

Any combination of ring electrodes 220 and segmented electrodes 230 may be disposed on the lead 200. For example, the lead may include a first ring electrode, two sets of segmented electrodes, each set formed of three segmented electrodes 230, and a final ring electrode at the end of the lead. This configuration may simply be referred to as a 1-3-3-1 configuration. It may be useful to refer to the electrodes with this shorthand notation. Thus, the embodiment of FIG. 3A may be referred to as a 1-1-3-3 configuration, while the embodiment of FIG. 3B may be referred to as a 3-3-1-1 configuration. Other eight-electrode configurations include, for example, a 2-2-2-2 configuration, where four sets of segmented electrodes are disposed on the lead, and a 4-4 configuration, where two sets of segmented electrodes, each having four segmented electrodes 230 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 4:
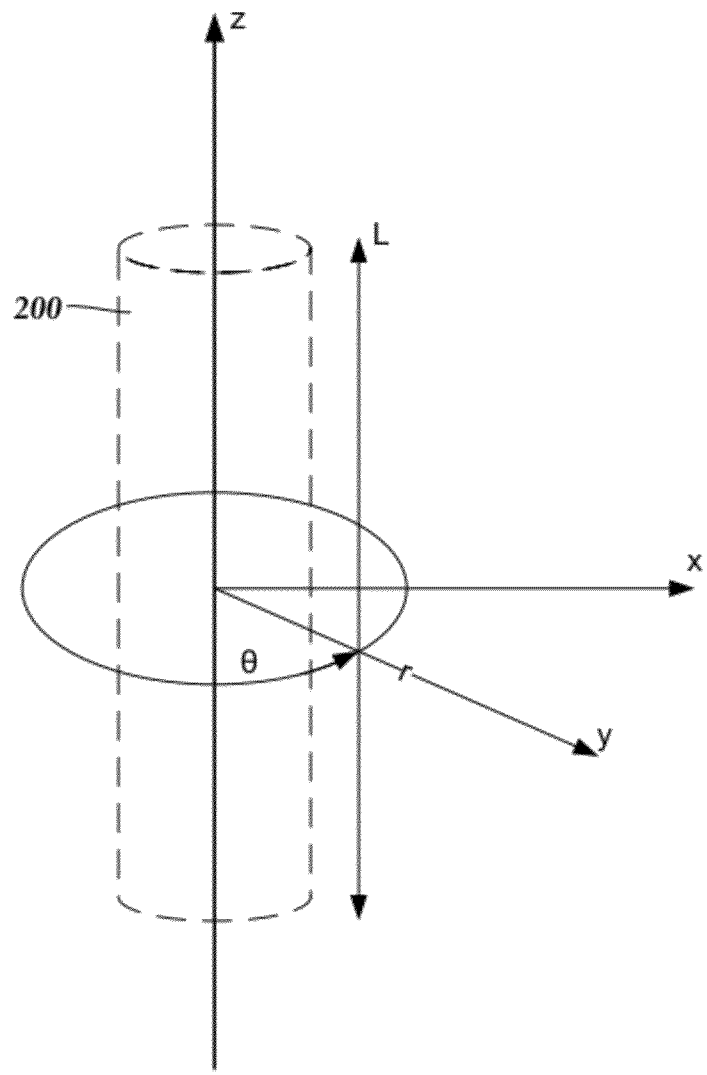
FIG. 4 is a schematic diagram of radial current steering along various electrode levels along the length of a lead, according to the invention.

FIG. 4 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle $\theta$ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 4, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 200 includes a plurality of sets of segmented electrodes 230, it may be desirable to form the lead 200 such that corresponding electrodes of different sets of segmented electrodes 230 are radially aligned with one another along the length of the lead 200 (see e.g., the segmented electrodes 230 shown in FIG. 2). Radial alignment between corresponding electrodes of different sets of segmented electrodes 230 along the length of the lead 200 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 200 are radially aligned with one another and do not radially shift in relation to one another during manufacturing of the lead 200.

Figure 5:
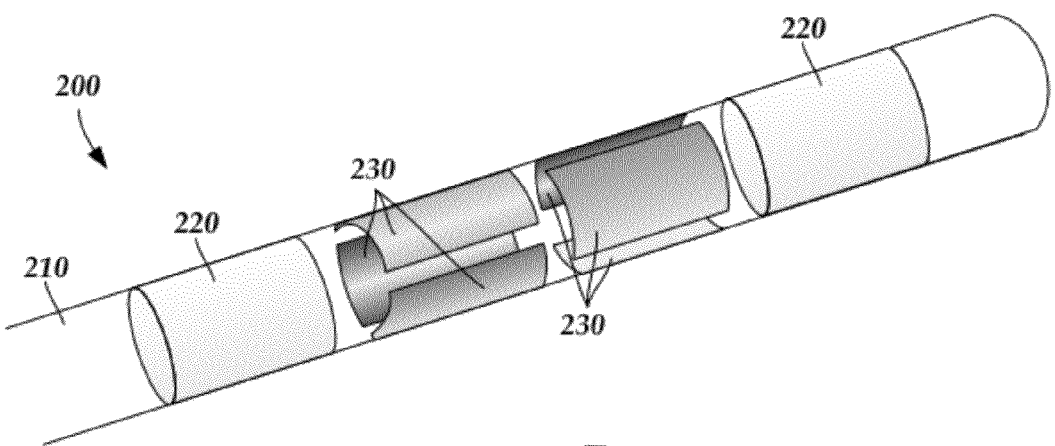
FIG. 5 is a perspective view of another embodiment of a portion of a lead having a plurality of segmented electrodes arranged in a staggered orientation, according to the invention.

FIG. 5 is a side view of another embodiment of the lead 200 having a plurality of sets of segmented electrodes. As shown in FIG. 5, individual electrodes in the two sets of segmented electrodes 230 are staggered relative to one another along the length of the lead body 210. In some cases, the staggered positioning of corresponding electrodes of different sets of segmented electrodes along the length of the lead 200 may be designed for a specific application.

Typically, the lead body is made of a transparent or translucent material. It may be difficult to visually distinguish individual segmented electrodes when the lead body is transparent or translucent. Visual identification of the segmented electrodes may be useful so that a practitioner can verify that the lead has segmented electrodes or to align the segmented electrodes along a desired orientation for implantation.

Figure 6A:
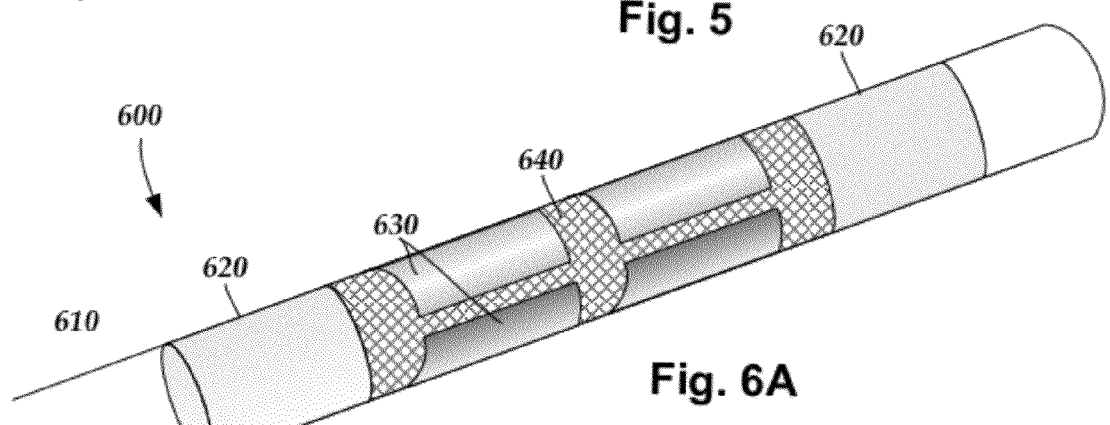
FIG. 6A is a perspective view of an embodiment of a portion of a lead having a plurality of segmented electrodes and opaque material between the electrodes, according to the invention.

To facilitate visual identification of segmented electrodes, a portion of the lead body between or around the segmented electrodes can be opaque, preferably white or a light color. FIG. 6A is a side view of an embodiment of a lead 600 with segmented electrodes 630 and ring electrodes 620 along the length of a lead body 610. A portion 640 of the lead body 610 between the electrodes 630, 620 is made of an opaque material so that the segmented electrodes 630 can be visually identified. The remainder of the lead body (i.e., the portions not cross-hatched in FIG. 6) can be transparent or translucent. The opacity of the portion 640 of the lead body may be limited to the surface of the lead body in portion 640 or may extend partially or completely through portion 640 of the lead body.

The opacity of portion 640 of the lead body may be generated using materials or processing techniques or combinations thereof. For example, the portion 640 of the lead body may include a biocompatible colorant or other opaque material, such as, for example, titanium dioxide, barium sulfate, or white polyethylene. This colorant or other opaque material may be used in combination with other materials to form the lead body or may be the sole material that forms the portion 640 of the lead body. As another example, the portion 640 of the lead body may be colored by a processing technique, such as laser marking or scoring, heating, grinding, or any combination thereof, to generate an opaque region.

Region 640 may have any suitable color. Preferably, the color of region 640 is a light color, such as, for example, white, off-white, or a pastel color. Preferably, the opaque region is less visibly reflective than the electrodes 630, 620 and, more preferably, the opaque region is substantially non-reflective. In at least some embodiments, roughening the surface of the opaque region, such as grinding or scoring the surface, may reduce reflectivity of the opaque region.

The region 640 of the lead body may have the same durometer or hardness as other portions of the lead body, or the region 640 may have a higher or lower durometer or hardness compared to other portions of the lead body.

Figure 6B:
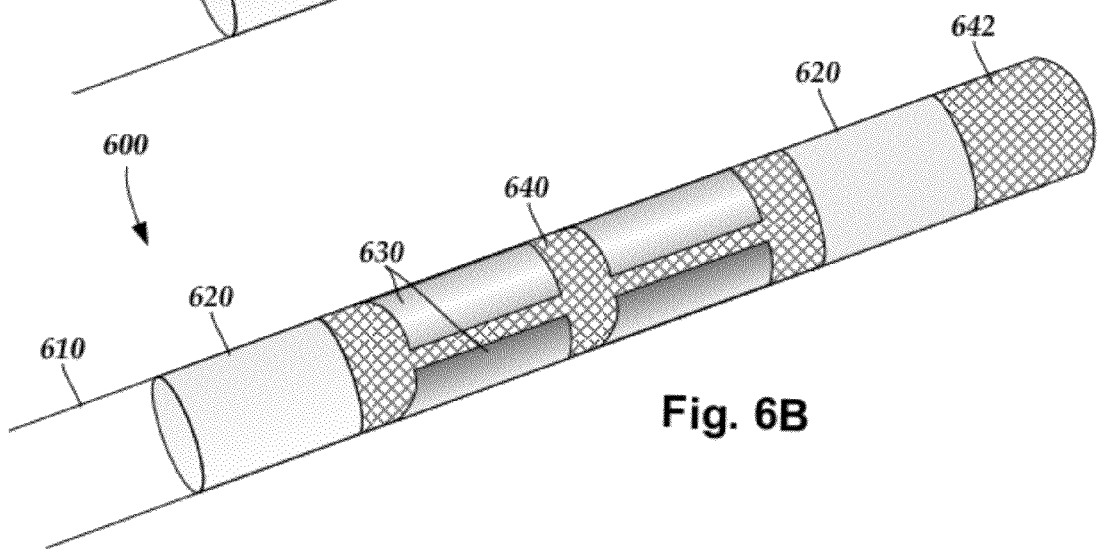
FIG. 6B is a perspective view of another embodiment of a portion of a lead having a plurality of segmented electrodes and opaque material between the electrodes and at a tip of the lead, according to the invention.

The embodiment of FIG. 6A illustrates one example of an arrangement of an opaque region with respect to segmented electrodes. In other embodiments, more or less of the lead body may be opaque. FIG. 6B illustrates another embodiment in which a tip region 642 is also opaque.

Figure 6C:
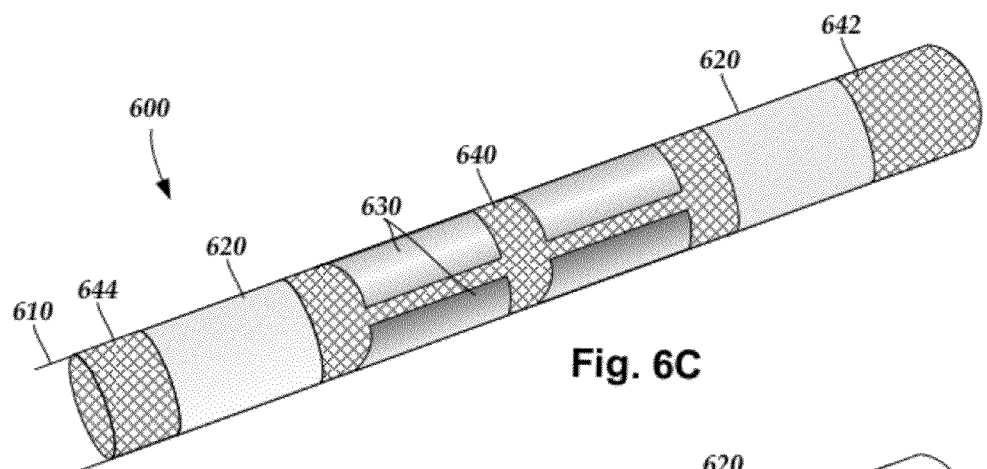
FIG. 6C is a perspective view of a third embodiment of a portion of a lead having a plurality of segmented electrodes and opaque material between the electrodes, at a distal tip of the lead, and proximal to the electrodes, according to the invention.
Figure 6D:
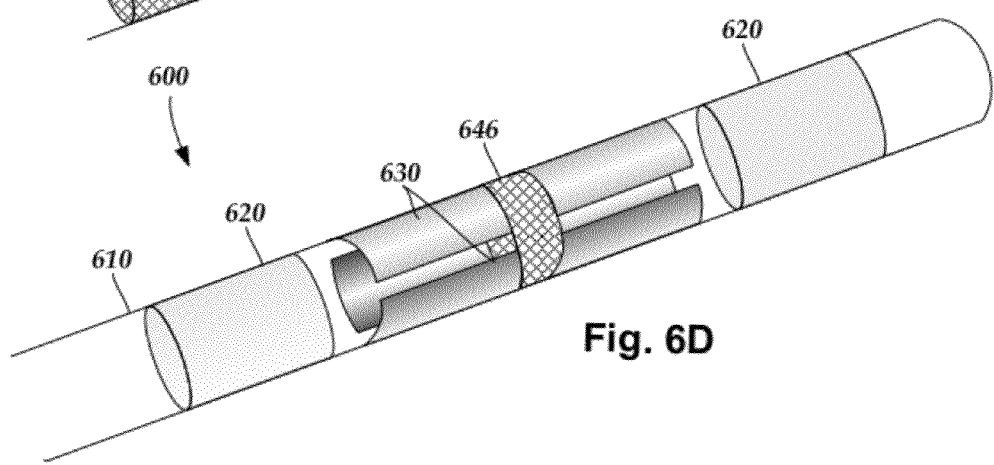
FIG. 6D is a perspective view of a fourth embodiment of a portion of a lead having a plurality of segmented electrodes and opaque material between the sets of segmented electrodes, according to the invention.
Figure 6E:
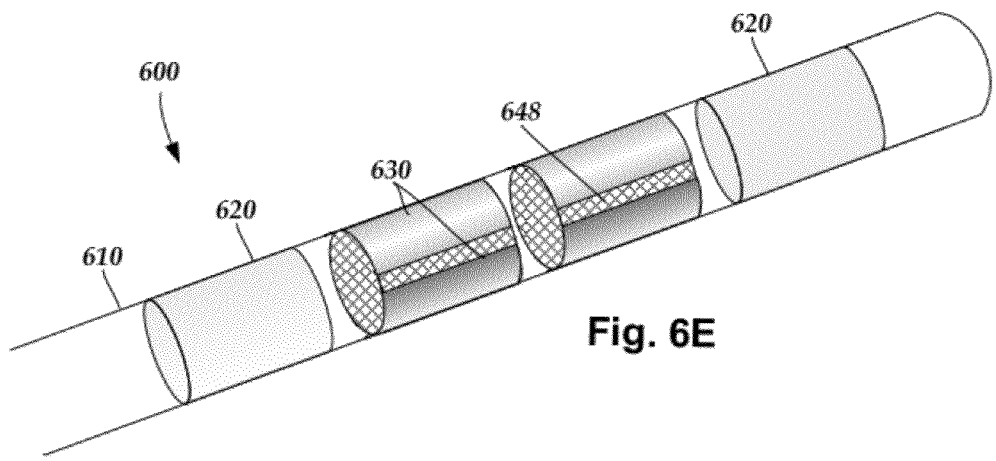
FIG. 6E is a perspective view of another embodiment of a portion of a lead having a plurality of segmented electrodes and opaque material between the segmented electrodes of each set, according to the invention.

FIG. 6C illustrates yet another embodiment in which the tip region 642 and region 644 proximal to the electrodes 630, 620 is also opaque. FIG. 6D illustrates a further embodiment in which only the region 646 between the sets of segmented electrodes is opaque. FIG. 6E is yet another embodiment in which only the region 648 between segmented electrodes of each set is opaque. It will be understood that the embodiments of FIGS. 6D and 6E can be combined so that both regions 646 and 648 are opaque. It will be further understood that the selection of opaque regions illustrated in FIGS. 6A-6E can also be applied other arrangements of segmented electrodes and optional ring electrodes.

Figure 7A:
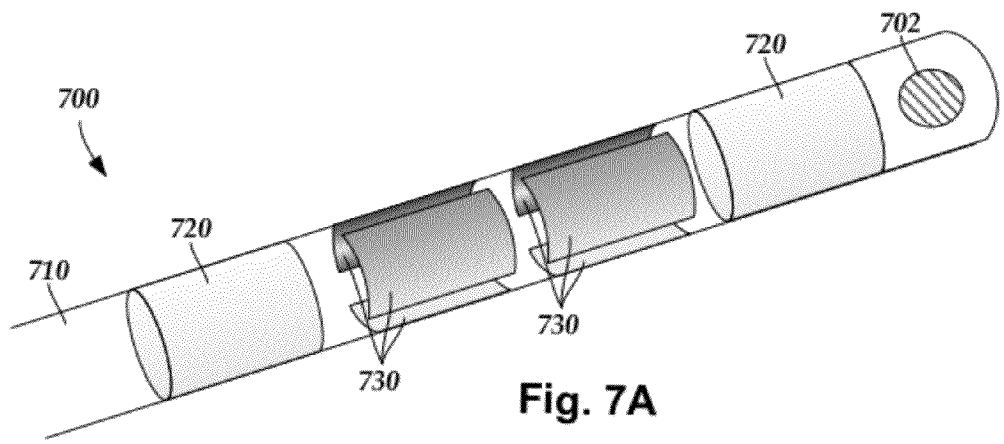
FIG. 7A is a perspective view of one embodiment of a portion of a lead having a plurality of segmented electrodes and a marker at a distal tip of the lead, according to the invention.
Figure 7B:
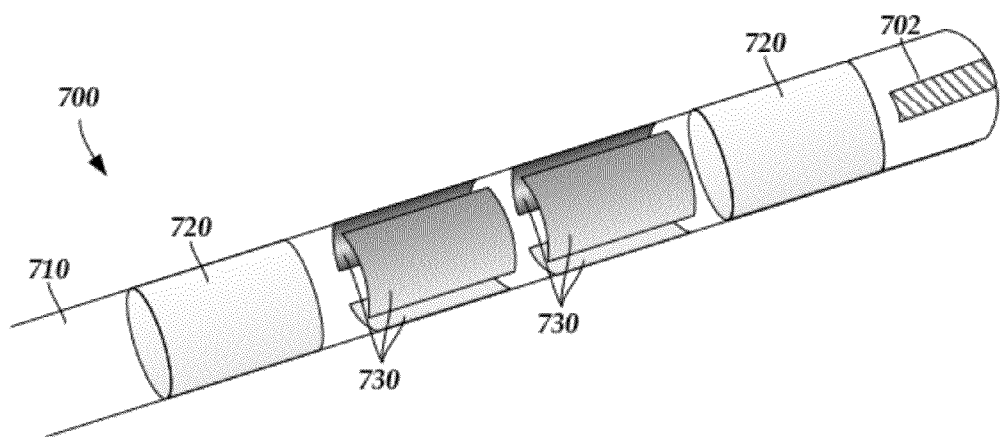
FIG. 7B is a perspective view of another embodiment of a portion of a lead having a plurality of segmented electrodes and a marker at a distal tip of the lead, according to the invention.

Another technique for indicating orientation or position of the segmented electrodes includes providing a mark at or near the distal end of the lead, and distal to all of the electrodes, to indicate the position of at least one of the segmented electrodes. As an example, FIGS. 7A and 7B illustrate leads 700 with segmented electrodes 730, optional ring electrodes 720, and a lead body 710. The lead 700 also includes a marking 702 at the distal tip 704 of the lead that is aligned with one of the segmented electrodes 730a. This marking may also align with one of the segmented electrodes in two sets of segmented electrodes, as illustrated in FIGS. 7A and 7B. It will be recognized that the marking can be aligned, if desired, with electrodes in more than two sets of segmented electrodes when the lead contains more than two sets.

The marking 702 may take any form including a circle (FIG. 7A), line (FIG. 7B), triangle, number, or any other regular or irregular shape or symbol. The marking may be formed using a colorant provided during or after formation of the lead body, an item inserted in the lead body, or by processing techniques such as, for example, laser scoring or marking, etching, grinding, or otherwise roughening the surface. A colorant may be provided on the surface or within the lead body or any combination thereof. The marking may be any suitable color, preferably, white, off-white, or some other light color. Optionally, the marking is radio-opaque.

In some embodiments, more than one marking is provided at the distal tip with each marking aligned with a different segmented electrode or electrodes. In some embodiments, a corresponding marking or markings may be provided at the proximal end of the lead and aligned with the marking or markings at the distal end of the lead.

Other arrangements for marking the lead body can be used. FIG. 8A-8F illustrate leads 800 with segmented electrodes 830, optional ring electrodes 820, and a lead body 810. These leads include a stripe 850 that extends along portions of the lead body near a distal end of the lead. The stripe is aligned with at least one segmented electrode and may be aligned with a segmented electrode in two or more sets of segmented electrodes as illustrated in FIGS. 8A-8F. Optionally, the stripe may extend to a proximal portion of the lead and may even extend to, or near, a proximal end of the lead.

Figure 8A:
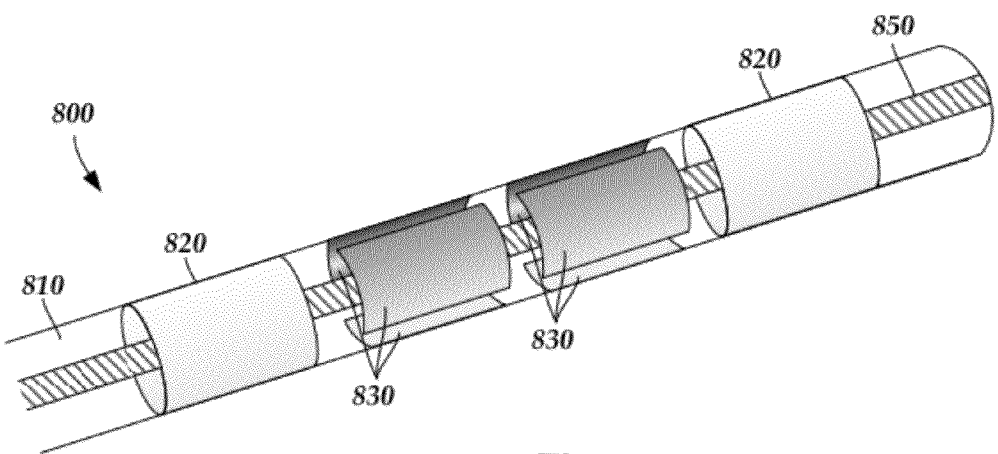
FIG. 8A is a perspective view of one embodiment of a portion of a lead having a plurality of segmented electrodes and a stripe extending along at least a distal portion of the lead, according to the invention.
Figure 8B:
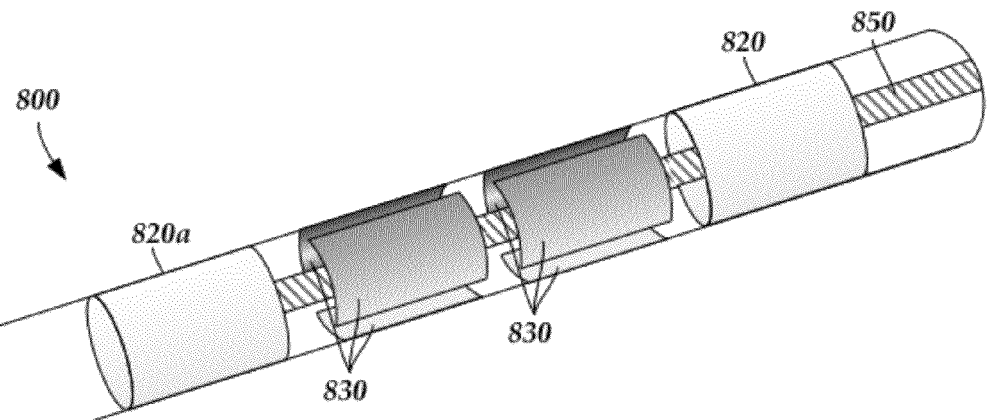
FIG. 8B is a perspective view of another embodiment of a portion of a lead having a plurality of segmented electrodes and a stripe extending along a distal portion of the lead, according to the invention.
Figure 8C:
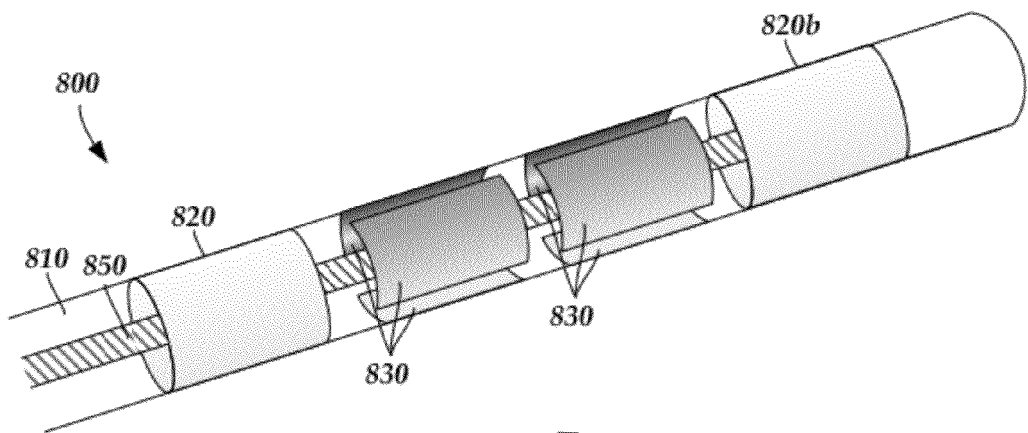
FIG. 8C is a perspective view of a third embodiment of a portion of a lead having a plurality of segmented electrodes and a stripe extending along at least a distal portion of the lead, according to the invention.
Figure 8D:
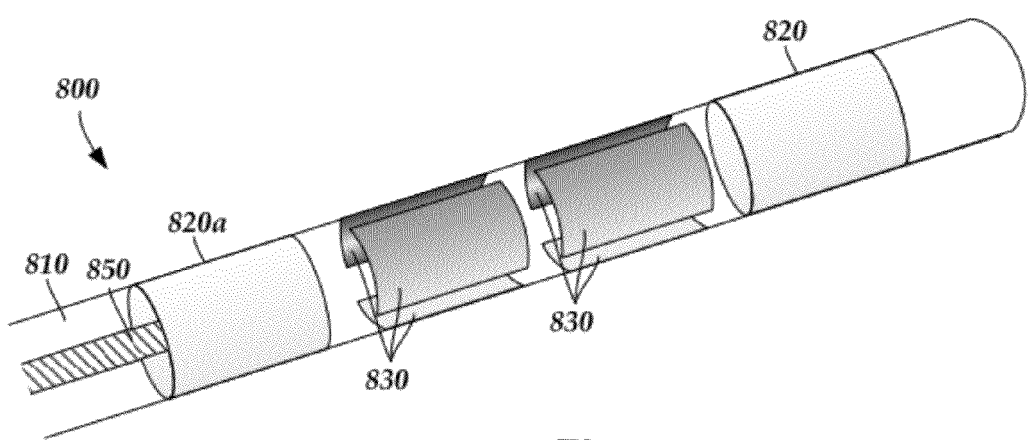
FIG. 8D is a perspective view of a fourth embodiment of a portion of a lead having a plurality of segmented electrodes and a stripe extending along a portion of the lead proximal to the electrodes, according to the invention.
Figure 8E:
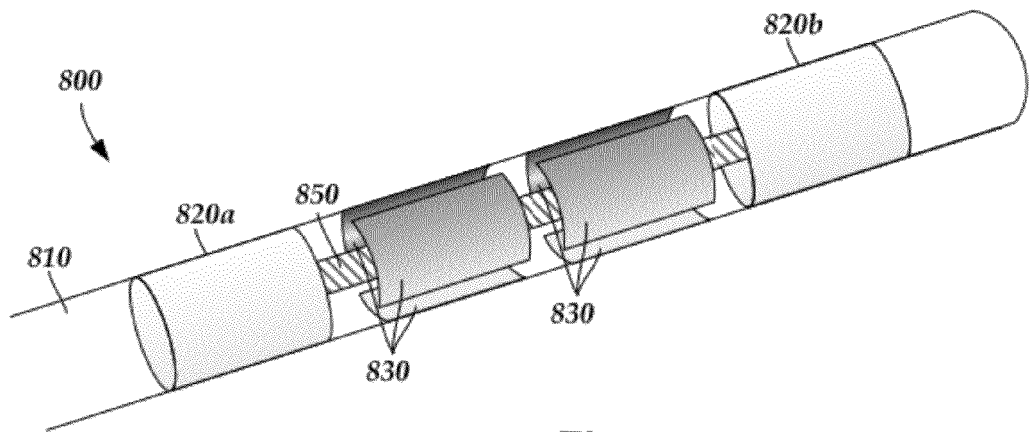
FIG. 8E is a perspective view of a fifth embodiment of a portion of a lead having a plurality of segmented electrodes and a stripe extending between electrodes at a distal portion of the lead, according to the invention.
Figure 8F:
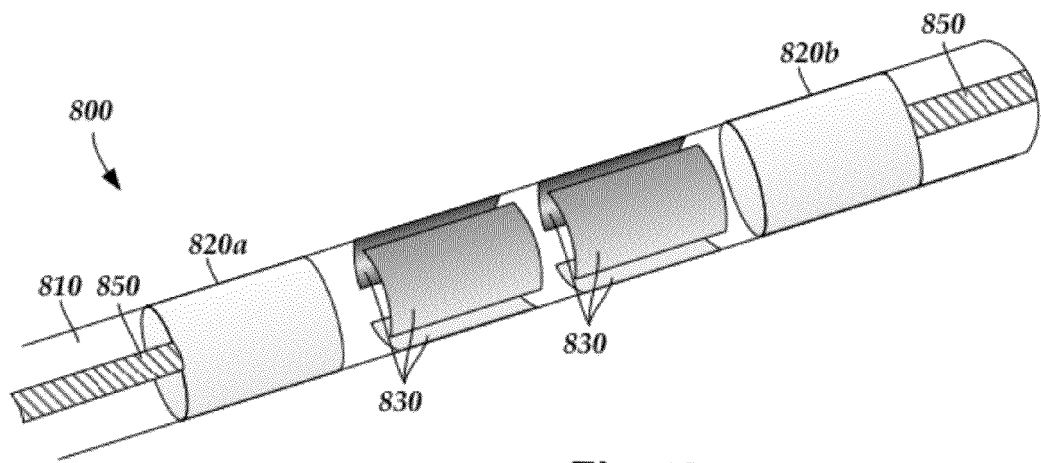
FIG. 8F is a perspective view of a sixth embodiment of a portion of a lead having a plurality of segmented electrodes and a stripe extending along portions of the lead proximal and distal to the electrodes, according to the invention.

In FIG. 8A, the stripe 850 extends along the lead body 810 from a distal tip to a location proximal of the electrodes 820, 830 of the lead 800. In FIG. 8B, the stripe 850 extends from the distal tip to the most proximal electrode 820*a*. In FIG. 8C, the stripe 850 extends from the most distal electrode 820*b* to a location proximal to the electrodes 820, 830. In FIG. 8D, the stripe 850 extends proximally from the most proximal electrode 820*a*. In FIG. 8E, the stripe 850 extends from the most distal electrode 820*b* to the most proximal electrode 820*a*. In FIG. 8F, the strip 850 extends distally from the most distal electrode 820*b* and proximally from the most proximal electrode 820*a*, but not between the electrodes.

The stripe may be formed using a colorant or by processing techniques such as, for example, laser scoring or marking, etching, grinding, or otherwise roughening the surface. A colorant may be provided on the surface or within the lead body or any combination thereof. The stripe may be any suitable color, preferably, white, off-white, or some other light color. Optionally, the strip is radio-opaque.

In some embodiments, more than one stripe may be used. In such embodiments, the different stripes may have different colors and are associated with different segmented electrodes. For example, a lead may have a stripe of a first color associated with the first segmented electrode in one or more (or even all) sets of segmented electrodes and another stripe of a second color associated with the second segmented electrode in one or more (or even all) sets of segmented electrodes. Additional stripes could be used for the third, fourth, or fifth electrodes and so on.

Figure 10A:
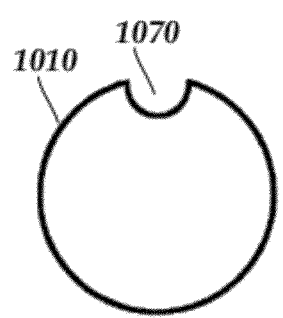
FIG. 10A is a cross-sectional view of one embodiment of a portion of a lead body having a groove or notch, according to the invention.
Figure 10B:
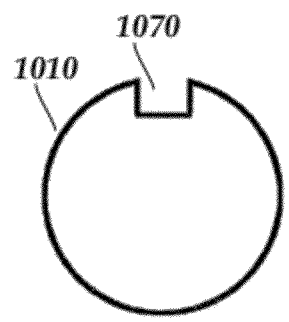
FIG. 10B is a perspective view of another embodiment of a portion of a lead body having a groove or notch, according to the invention.

Alternatively, instead of a stripe, a groove or notch may be used and positioned at the same locations as stripe 850 in any of FIGS. 8A-8F. FIGS. 10A and 10B are schematic cross-sectional illustrations of embodiments of a lead body 1010 with a groove or notch 1070 formed in the exterior surface of the lead body. The groove or notch may be formed during or after generation of the lead body. The groove or notch may have any cross-sectional shape including, but not limited, circular (e.g., FIG. 10A), square (e.g., FIG. 10B), triangular, and the like. Optionally, the groove or notch may be colored.

Figure 9:
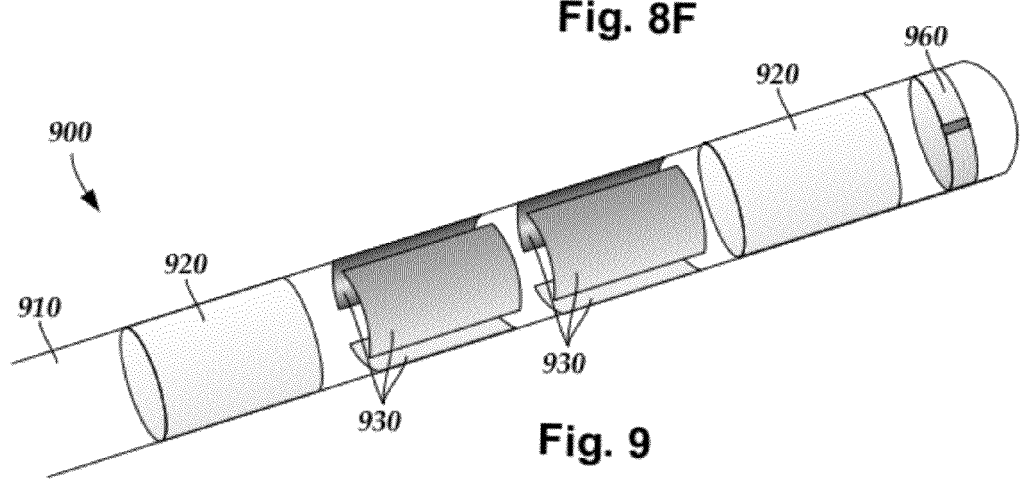
FIG. 9 is a perspective view of one embodiment of a portion of a lead having a plurality of segmented electrodes and an indicator ring on a distal portion of the lead, according to the invention.

FIG. 9 illustrates a lead 900 with segmented electrode 930, optional ring electrodes 920, a lead body 910, and an indicator ring 960. The indicator ring 960 is marked to indicate a particular segmented electrode or particular segmented electrodes in two or more sets of segmented electrodes. The indicator ring 960 may be marked in any suitable manner including, but not limited to, scoring, etching, engraving, removing a portion of the ring, and the like. The indicator ring 960 may be made of any suitable biocompatible material including metals, polymers, and ceramics. The indicator ring may be radio-opaque.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulation lead, comprising:
   a non-conductive lead body comprising a longitudinal surface, a distal end, and a proximal end; and
   a plurality of electrodes disposed along the longitudinal surface of the lead body near the distal end of the lead body, the plurality of electrodes comprising a plurality of segmented electrodes;
   wherein at least a first portion of the lead body, proximal to the plurality of electrodes, is transparent or translucent and at least a second portion of the lead body, separating two or more of the segmented electrodes, is visibly opaque so that the segmented electrodes separated by the second portion of the lead body are visually distinct upon direct observation of the segmented electrodes and second portion of the lead body.

2. The stimulation lead of claim 1, wherein at least some of the segmented electrodes are formed into a first set of segmented electrodes comprising at least two of the segmented electrodes disposed around a circumference of the lead at a first longitudinal position along the lead, and a second set of segmented electrodes comprising at least two of the segmented electrodes disposed around a circumference of the lead at a second longitudinal position along the lead.

3. The stimulation lead of claim 2, wherein the second portion of the lead body comprises a region between at least two of the segmented electrodes of the first set of segmented electrodes.

4. The stimulation lead of claim 2, wherein the second portion of the lead body comprises a region between at least one of the segmented electrodes of the first set of segmented electrodes and at least one of the segmented electrodes of the second set of segmented electrodes.

5. The stimulation lead of claim 4, wherein the second portion of the lead body farther comprises a region between at least two of the segmented electrodes of the first set of segmented electrodes.

6. The stimulation lead of claim 1, wherein the second portion of the lead body comprises a tip region at the distal end of the lead body.

7. The stimulation lead of claim 1, wherein the plurality of electrodes further comprises at least one ring electrode.

8. The stimulation lead of claim 7, wherein at least some of the segmented electrodes are formed into a first set of segmented electrodes comprising at least two of the segmented electrodes disposed around a circumference of the lead at a first longitudinal position along the lead, and a second set of segmented electrodes comprising at least two of the segmented electrodes disposed around a circumference of the lead at a second longitudinal position along the lead and wherein the second portion of the lead body comprises a region between the first set of segmented electrodes and a one of the at least one ring electrode.

9. The stimulation lead of claim 7, wherein the at least one ring electrode comprises a first ring electrode located distal to the plurality of segmented electrodes and a second ring electrode located proximal to the plurality of segmented electrodes, wherein the second portion of the lead body comprises a region between the first ring electrode and the second ring electrode.

10. The stimulation lead of claim 1, wherein the second portion of the lead body comprises a region proximal to the plurality of electrodes.

11. The lead of claim 1, wherein the second portion of the lead body has a white or light color.

12. The lead of claim 1, wherein the second portion of the lead body has a white, off-white, or pastel color.

13. The lead of claim 1, wherein the second portion of the lead body is rendered opaque by laser marking or scoring or grinding the second portion of the lead body.

14. The lead of claim 1, wherein the second portion of the lead body is less reflective than the segmented electrodes.

15. The lead of claim 14 wherein the second portion of the lead body has a roughened surface to reduce reflectivity.

* * * * *